United States Patent [19]

Murphy et al.

[11] 4,346,055

[45] Aug. 24, 1982

[54] AUTOMATIC IGNITION SYSTEM FOR A FLAME IONIZATION DETECTOR

[75] Inventors: Andrew J. Murphy, West Grove, Pa.; Robert P. Rhodes, Newark, Del.; Terry A. Woodruff, Kennett Square, Pa.

[73] Assignee: Hewlett-Packard Company, Palo Alto, Calif.

[21] Appl. No.: 159,034

[22] Filed: Jun. 13, 1980

Related U.S. Application Data

[63] Continuation of Ser. No. 964,753, Nov. 29, 1978, abandoned.

[51] Int. Cl.³ ...................... G01N 21/72; G01N 27/62
[52] U.S. Cl. .................................... 422/54; 23/232 E
[58] Field of Search ............... 422/54, 105, 108, 109; 23/232 E

[56] References Cited

U.S. PATENT DOCUMENTS

| | | | |
|---|---|---|---|
| 3,340,013 | 9/1967 | Rooney et al. | 422/54 |
| 3,423,181 | 1/1969 | Dimick et al. | 422/54 |
| 3,597,162 | 8/1971 | Reinecke | 422/54 |
| 3,827,859 | 8/1974 | Vitzthum | 422/54 |
| 3,920,401 | 11/1975 | Gatiss | 422/54 |
| 3,985,509 | 10/1976 | Trone | 422/54 |

Primary Examiner—Michael S. Marcus
Attorney, Agent, or Firm—Donald N. Timbie

[57] ABSTRACT

Apparatus for igniting a flame ionization detector wherein means are provided for gradually reducing the flow of oxygen to the jet in response to a sudden increase in the temperature at a point downstream from the jet and wherein normal oxygen flow is restored after the temperature decreases to an operating value.

5 Claims, 2 Drawing Figures

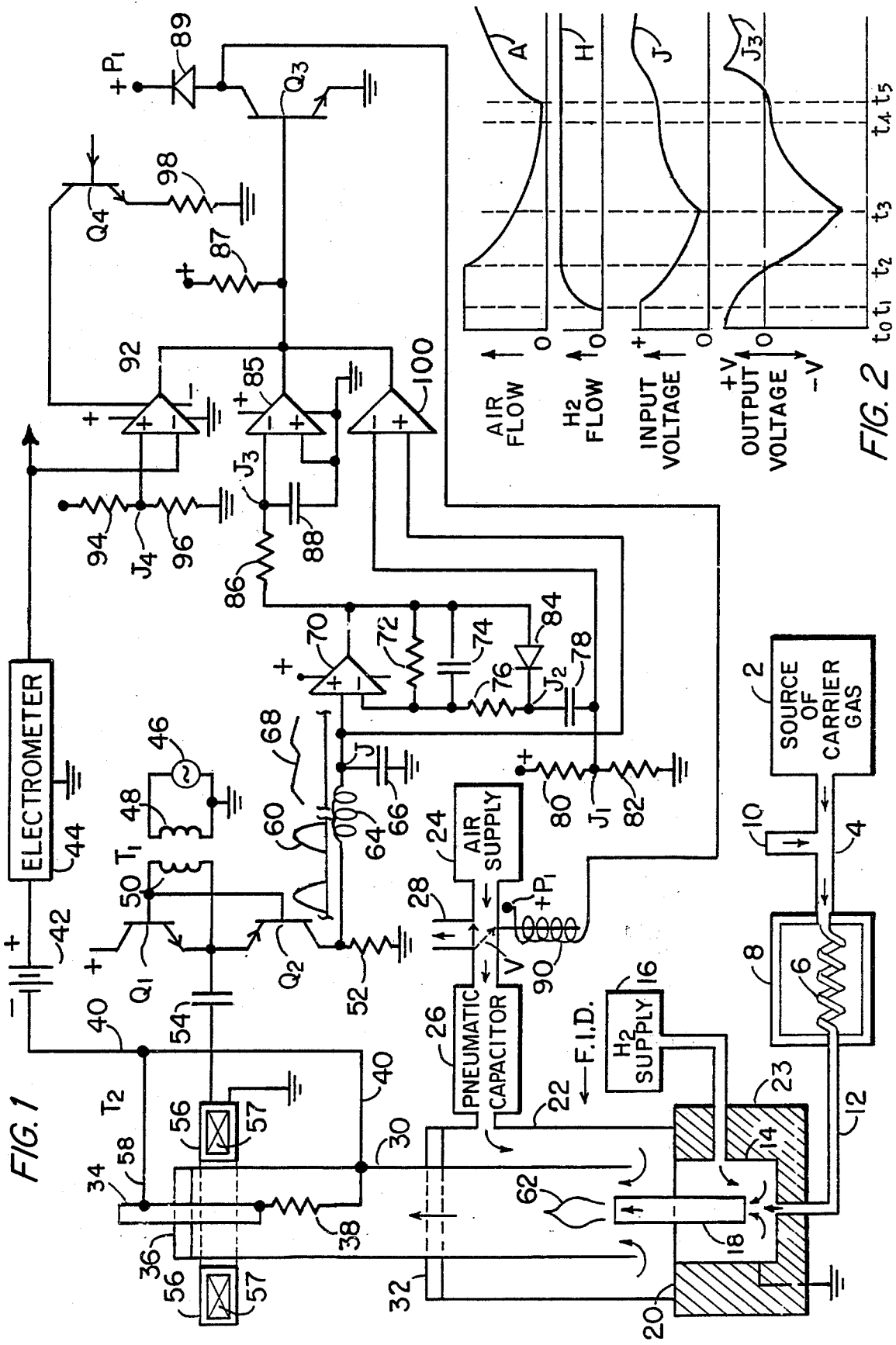

4,346,055

AUTOMATIC IGNITION SYSTEM FOR A FLAME IONIZATION DETECTOR

CROSS REFERENCE TO RELATED APPLICATION

This is a continuation of application Ser. No. 964,753, filed Nov. 29, 1978, abandoned.

BACKGROUND OF THE INVENTION

Flame ionization detectors operate by burning the material to be analyzed so as to form ions and measuring the current that is produced when the ions are collected. When used with a gas chromatograph, the gases eluting from the column are mixed with hydrogen or some other highly flammable gas and passed through a tube to form a jet. Air is introduced at the periphery of the jet so as to form a stable flame when the jet is ignited. A collector tube is placed adjacent to the jet, a source of direct current voltage and an electrometer are connected in circuit with the tubes so as to collect the ions formed in the flame and produce a current in the electrometer that is proportional to the rate at which the ions are collected.

When used with a chromatograph in which the sequence of operations is controlled by an attendant, the jet can be ignited with manual means whenever required and it can be reignited if the jet flames out, but when the detector is used in a chromatograph that operates in response to a software program, it is essential that initial ignition of the jet, as well as its re-ignition, be achieved by automatic means.

BRIEF DESCRIPTION OF THE INVENTION

The way in which initial ignition and re-ignition of the jet may be automatically achieved in accordance with this invention may be briefly explained as follows. A hot filament or other means for igniting gases is mounted at a point in the collector tube that is downstream from the jet. As the gases to be analyzed and the hydrogen emerge in the jet, they start mixing with the air that is normally introduced around its periphery. When the gases reach the hot filament at the downstream end of the collector tube, they are combusted. The normal amount of air flow is such that the resulting flame front is unable to propagate with sufficient speed to move upstream toward the jet. Therefore, means are provided for gradually reducing the flow of air, and hence the velocity of the gases flowing toward the filament, below its normal value in response to the rapid increase in temperature caused by the combustion referred to. When the air-to-hydrogen ratio is thereby reduced to a certain value, the flame front propagates at a sufficiently greater speed to move upstream in the slower moving gases and ignite the jet. At this point, the air flow is increased to its normal value. Once lit, the flaming jet remains in position, but should it flame out for any reason, the process is repeated.

The temperature at the downstream end of the collector tube may be sensed by means that are entirely separate from the filament, but in accordance with another aspect of this invention, the filament is used for this purpose. Briefly, this is accomplished by inserting a temperature sensing resistor in the circuit that supplies electrical power to the filament. As the resistance of the filament changes with temperature, the current flowing in the resistor changes and produces a voltage thereacross that is related to the temperature.

Under some conditions, such as when certain chemicals momentarily appear in the gases supplied to the jet, the flame may become sufficiently large and hot to change the temperature in the vicinity of the filament by a sufficient amount to cause the apparatus to operate as though the flame had gone out. As the resulting reduction in the supply of air to the detector would interfere with the measurements being made, disabling means are provided for preventing a reduction in the flow of air as long as the output current supplied by the detector is in excess of some predetermined value, such as 50 pA, which indicates that the jet has not flamed out. If, as may sometimes be desired, the detector is deliberately disabled, its output current will be unknown and therefore possibly greater than the predetermined value just referred to, so that the auto ignition system could not operate. Operation under these conditions can be attained by disabling the disabling means.

In order to measure the rate of air flow in the detector, it is generally desirable to disable the igniter, but inasmuch as the circuits employed would therefore respond so as to reduce the flow of air, means are provided for preventing this from occurring.

DESCRIPTION OF THE DRAWING

FIG. 1 is a schematic representation of a preferred embodiment of the invention, and FIG. 2 is a series of graphs used in explaining the operation of FIG. 1.

CHROMATOGRAPH AND DETECTOR

In FIG. 1, a regulated flow of carrier gas is supplied by a source 2 via a tube 4 to the input of a chromatographic column 6 that is mounted within a temperature-controlled oven 8. A measured quantity of the chemicals to be analyzed is inserted into the stream of carrier gas flowing in the tube 4 by a sample injector 10. The gases eluting from the column 6 are conducted via a tube 12 to the bottom of an electrically grounded first mixing chamber 14 of a flame ionization detector (FID) where they are mixed with hydrogen supplied to the top of the chamber from a regulated source 16. The flame ionization detector FID is shown in vertical cross-section. A jet tube 18 that extends through the upper wall 20 of the chamber 14 to a point near its bottom conducts the mixture of hydrogen and elutant into the bottom of a second metal mixing chamber 22 where they mix with air supplied to the top of the chamber 22. The mixing chamber 14 is contained in a means 23 for setting the temperature at a desired value.

In accordance with the invention, and for reasons that will be subsequently explained, air supplied by a flow-regulated supply 24 passes through a normally open valve V into a limited volume represented by a pneumatic capacitor 26, which is actually a tank of small volume, and from there into the upper portion of the mixing chamber 22. It will be understood that air supply as used herein includes any means for supplying oxygen. When the valve V is moved by circuits to be described from the position indicated by the solid line to the position indicated by the dotted line, air flows out of a vent 28 to the atmosphere, and the input to the pneumatic capacitor 26 is closed. As the flow of air supplied to the second mixing chamber 22 can now only come from the pneumatic capacitor 26, it decreases exponentially toward zero. The time required to reach zero may vary, but two seconds has been found satisfactory. If the volume of tubing between the valve V and the mixing chamber 22 is negligible, some additional volume may be supplied by a tank such as indicated at 26 or it may be supplied by adding tubing. The term pneumatic capacitor means all the volume from which air may flow to the mixing chamber 22 when the valve V is closed.

A metal collector tube 30 that is larger in diameter than the jet tube 18 passes through a collar 32 of electrical insulating material, which is located at the upper end of the second mixing chamber 22, and extends downwardly far enough to overlap the upper end of the jet tube 18. Air from the pneumatic capacitor 26 flows downwardly in the annular space between the collector tube 30 and the mixing chamber 22 and then upwardly on the inside of the collector tube 30 so as to mix with the hydrogen, sample, and carrier gases emerging from the jet tube 18. A metal exit tube 34 extends into the upper end of the collector tube 30, and the annular space between the tubes is closed by a collar 36 of electrical insulating material. A filament 38 is connected between the inner end of the exit tube 34 and the collector tube 30. If the latter is to collect positive ions, it is connected via a lead 40 to the negative terminal of a power supply, herein schematically illustrated by a battery 42. The positive terminal of the battery 42 is connected to the input of an electrometer 44. The rate at which positive ions arrive at the negative collector tube 30 determines the current that flows in the electrometer 44 so that the current is proportional to the mass flow rate of the particular constituent of the sample gas that is flowing through the flaming jet at any time. Integration of this current therefore indicates the total mass of the constituent.

FILAMENT HEATING AND TEMPERATURE SENSING CIRCUIT

A source 46 of alternating current that is referenced to ground is coupled across a primary winding 48 of a transformer $T_1$. One end of the secondary winding 50 is connected to the base of an NPN transistor $Q_1$ and also to the base of a PNP transistor $Q_2$. The collector of $Q_1$ is connected to a point of positive potential, its emitter is connected to the emitter of the transistor $Q_2$, and the collector of $Q_2$ is connected to ground via a current sensing resistor 52. The other end of the secondary winding 50 of the transformer $T_1$ is connected to the emitters of $Q_1$ and $Q_2$. A coupling capacitor 54 is connected between the emitters of $Q_1$ and $Q_2$ and one end of a primary winding 56 of a transformer $T_2$ that is wound on a magnetic core 57. The other end of the winding 56 is connected to ground. The secondary winding of the transformer $T_2$ is a single loop comprised of the exit tube 34, the filament 38, the lead 40, and an additional lead 58 that is connected between the exit tube 34 and the lead 40. The lead 58 is only required to complete the loop so that it encircles the transformer core 57. The filament 38 is thus part of the secondary winding. During one half-cycle of the alternating current provided by the source 46, $Q_1$ conducts and $Q_2$ is turned off; and during the next half-cycle, $Q_1$ is turned off and $Q_2$ is turned on so as to cause a reversal of current in the primary winding 56 of the transformer $T_2$. The amplitude of the half-cycles of current that flow through the transistor $Q_2$ and the resistor 52 produces half-cycles of voltage across the resistor 52 such as indicated at 60 having an amplitude that is inversely proportional to the resistance of the filament 38 and therefore inversely proportional to the temperature of the gases passing by it.

TEMPERATURE CHANGE SENSING CIRCUIT

When the jet from the jet tube 18 is not burning, the hydrogen and elution gases mix with the air as they flow up the collector tube 30 so as to form a mixture that will be combusted when it reaches the hot filament 38. When this occurs, the temperature at the downstream or exit end of the collector tube 30 and the resistance of the filament 38 increase rapidly. Means to be described are provided for responding to this condition so as to gradually reduce the flow of air to the mixing chamber 22 and cause a flame front to move from the exit end of the collector tube 30 to the end surrounding the jet tube 18. This ignites the jet emanating from the jet tube 18 and forms a stationary flame, as indicated at 62.

Variations in the design of detectors cause considerable variation in the temperature of the gases at the exit end of the collector tube 30 when the jet is burning, and variations of the temperature at which the mixing chamber 14 is operated have a similar effect when the jet is not burning. It would therefore be difficult to select a single temperature that would give a positive indication as to whether the jet is burning or not. Whatever the temperature may be, however, it generally increases suddenly when the jet stops burning and decreases suddenly when the jet is ignited. Accordingly, means are provided for initiating the decrease in air flow to the detector in response to changes in temperature rather than to its actual value.

One means for operating in this manner will now be described. As previously stated, the amplitude of the pulses of voltage 60 produced across the resistor 52 is inversely proportional to the temperature of the filament 38. They are applied to a low pass filter comprised of an inductor 64 and a capacitor 66 connected in series to ground so that the voltage appearing at their junction J may be relatively smooth, as indicated at 68. This voltage is applied to the non-inverting input of an operational amplifier 70. A resistor 72 and a capacitor 74 are connected in parallel between the output of the amplifier 70 and its inverting input; and a resistor 76 and a capacitor 78 are connected in series in the order named between the inverting input and a point of positive potential such as the junction $J_1$ of resistors 80 and 82 that are connected between a point of higher positive potential and ground. The anode of a diode 84 is connected to the output of the amplifier 70, and its cathode is connected to the junction $J_2$ of the resistor 76 and the capacitor 78. The output voltage of the circuit appears at the junction $J_3$ of a resistor 86 and a capacitor 88 that are connected in series in the order named between the output terminal of the amplifier 70 and ground.

When the jet is not ignited, the amplitude of the pulses 60 and of the smoothed wave 68 derived from them is at a maximum positive value that is greater than the positive voltage at the junction $J_1$. The capacitor 78 is rapidly charged to this difference in voltage via the diode 84, and the output of the amplifier 70 is positive. When the ignition process is started, the gases at the upper end of the collector tube 30 start burning so as to raise the temperature of the filament 38 and lower the input voltage 68 below the voltage at the inverting input of the amplifier 70. Because of the thermal inertia of the filament 38, this may take a short time, but when the voltage finally drops below the voltage at the inverting input, the output voltage of the amplifier 70 becomes negative with respect to ground. It can be seen that changes in the input voltage 68 that are slow with respect to the RC time constant of the resistor 76 and the capacitor 78 will cause a corresponding change in the voltage at $J_2$ so that the output of the amplifier 70 remains unchanged. More rapid changes in the decrease of the input signal 68 will not be followed by the voltage at $J_2$ and will cause the output voltage of the amplifier 70 at $J_3$ to drop. Various time constants can be used, but one of approximately ten seconds has been found long enough to permit peaks of temperature produced in normal operation to occur without causing the ignition circuit to operate.

VALVE CONTROL CIRCUIT

Whenever the output voltage of the operational amplifier 70 and consequently the voltage at $J_3$ becomes negative, means such as the following are provided for moving the valve V to its dotted-line position, thereby closing the input to the pneumatic capacitor 26 and directing the air from the supply 24 to the atmosphere via the vent 28. The junction $J_3$ is connected to the inverting input of a comparator 85 having its non-inverting input connected to ground. The output of the comparator 85 is connected to a point of positive potential via a resistor 87 and to the base of an NPN transistor $Q_3$. The anode of a diode 89 is connected to the collector of $Q_3$, and the cathode of the diode 89 is connected to a point of positive potential $P_1$. The emitter of $Q_3$ is connected to ground. One end of a relay coil 90 that operates the valve V is connected to the point $+P_1$, and the other end is connected to the collector of $Q_3$. When its base is positive, $Q_3$ conducts so as to energize the coil 90 and place the valve V in the position indicated by the dotted line. When its base is negative, $Q_3$ does not conduct, the coil 90 is not energized, and the valve V is placed in its normal position indicated by the solid line.

OPERATION

In the following explanation of the operation of the illustrated embodiment of the invention, reference will be made to the graphs A, H, J and $J_3$ of FIG. 2 which respectively illustrate the variations with time of the rate of air flow into the mixing chamber 22, the rate of hydrogen flow into the mixing chamber 14, the input voltage at the junction J, and the output voltage at the junction $J_3$.

At $t_0$, the rate of air flow into the mixing chamber 22 is that which occurs when the valve V is in the solid-line position and the detector is operating in a normal manner. As indicated by the graph H, no hydrogen is flowing into the mixing chamber 14 at the time $t_0$ so that no burning occurs at the exit end of the collector tube 30. The temperature of the filament 38 is low and depends on the temperature of the gases in the jet at the upper end of the jet tube 18, and this in turn depends on the temperature in the zone 23. Under this condition, the voltage at the junction J is more positive than the voltage at the junction $J_1$, and the output terminal of the amplifier 70 is also at a positive voltage. The capacitor 78 is charged to the output voltage of the amplifier 70 via the diode 84, and the valve V is in the solid-line position.

At a time $t_1$, hydrogen from the supply 16 starts flowing into the mixing chamber 14. Shortly thereafter, combustion occurs at the exit or downstream end of the collector tube 30 and the temperature of the filament 38 and the value of its resistance start to increase. This decreases the load on the transformer $T_1$ and therefore the amplitude of the half-cycle pulses 60. As can be seen from the graph J, the voltage at the non-inverting input of the amplifier 70 becomes less positive and the voltage at its output terminal also reduces. The diode 84 is cut off and the capacitor 78 is discharged at a rate determined by RC time constant of the resistor 76 and the capacitor 78.

At the time $t_2$, the voltage at the junction J, which is connected to the non-inverting input of the amplifier 70, becomes less than the voltage at $J_2$ so that the voltage at its output terminal now becomes negative with respect to ground.

The output voltage of the circuit at the junction $J_3$ follows the voltage at the output terminal of the amplifier 70. Prior to the time $t_2$, it is positive with respect to ground so that the output of the comparator 85 is negative. At $t_2$, the voltage at $J_3$ becomes negative with respect to ground so that the output of the comparator 85 becomes positive. This causes $Q_3$ to conduct and energize the relay coil 90. The valve V is moved to its dotted-line position so as to close the input to the pneumatic capacitor 26 and direct air from the supply 24 to the atmosphere via the vent 28. The velocity with which the gases flow down the collector tube 30 is reduced.

With the valve V in this position, air for the mixing chamber 22 can only come from the pneumatic capacitor 26, and its rate of flow therefore decays exponentially after the time $t_2$, as indicated by the graph A. At some time $t_3$, the ratio of air to hydrogen reaches a value such that the flame front at the exit end of the collector tube 30 can advance with sufficient velocity to start moving upstream toward the jet at the end of the jet tube 18. At the time $t_4$, the flame front reaches the jet and ignites it. Between $t_3$ and $t_4$, the temperature and resistance of the filament 38 and the loading on the transformer decreases so as to cause the half-cycle of current flowing through the resistor 52 to increase in amplitude. As a result, the voltage at the junction J increases. When it once again exceeds the voltage at the upper end of the resistor 76, herein indicated as occurring at $t_5$, the output terminal of the amplifier 70, as well as the output voltage at the junction $J_3$, becomes positive with respect to ground. This turns $Q_3$ off, de-energizes the relay coil 90, and causes the valve V to revert to its normal solid-line position. The rate of flow of air into the mixing chamber 22 increases exponentially after $t_5$ as indicated by the graph A, and increases the cooling of the filament 38 until it reaches thermal equilibrium. The temperature of the filament occurring at this point may be different than it was prior to ignition when all gases are flowing down the collector tube 30 and there is no burning, but the circuit accommodates itself to this new steady state condition.

FALSE IGNITION

When the column 6 contains chemicals such as hexane, they often elute therefrom during a short period and cause the burning jet to increase in size and temperature sufficiently to change the temperature of the filament 38 by a significant amount. The circuit thus far described might respond to this change in the way it would when the burning of the jet ceases and a flame is ignited near the exit end of the collector tube 30. In order to prevent the reduction in supply air that would otherwise occur and interfere with the measurements being made, means are provided for inhibiting the ignition circuit and preventing the valve V from being operated as long as the current provided by the electrometer 44 exceeds some predetermined value, such as 50 pA, which indicates that the jet has not flamed out. In the embodiment shown, this function is performed by a comparator 92 having its non-inverting input connected to a point of negative potential such as the junction $J_4$ between the resistors 94 and 96 that are connected between a point of negative potential and ground. The inverting input is connected to the electrometer 44 so as to receive a negative voltage proportional to the current it provides. When the current is greater than the desired amount, the output voltage of the comparator 92 is zero so as to drive the base of $Q_3$, to which it is coupled, beyond cut-off. The current at which this occurs is set by the relative voltage between resistors 94 and 96. Inasmuch as $Q_3$ cannot conduct, the valve V cannot be moved.

Conditions exist, however, when it is desirable to disable the disabling circuit just described, as for example when the detector is turned off and it is desired that the auto ignition circuit be free to operate. A transistor $Q_4$ is provided for this purpose. Its emitter is grounded through a resistor 98, and its collector is connected to an input of the comparator 92 that causes the output of the comparator 92 to be open-circuited when $Q_4$ is made to conduct by application of a suitable voltage to its base.

MAINTENANCE OPERATION

In order to prevent the valve V from being moved from its normal or solid-line position, in the event that the ignition circuit is disconnected, as for example when the gas flows are being checked, a comparator 100 is used. Its inverting input is connected to the positive voltage at the junction $J_1$; its non-inverting input is connected to the non-inverting input of the amplifier 70; and its output is connected to the base of the transistor $Q_3$. If the igniter were disconnected, as for example by opening the primary circuit of $T_2$, the voltage at the non-inverting input of the amplifier 70 would drop just as though the ignition cycle were being initiated. This causes the output of the amplifier 70 to go negative and the output of the comparator 85 goes high. $Q_3$ would therefore conduct and energize the coil 90 so as to move the valve V to the dotted-line position except for the fact that the comparator 100 prevents this from occurring because its output goes negative so as to prevent $Q_3$ from conducting.

ALTERNATIVE EMBODIMENTS OF THE INVENTION

In the FID detector described, the jet 62 is of the diffusion type wherein air diffuses into the jet to form a combustible mixture that can form a stable flame when ignited. In other detectors, however, pre-mixed jets are used wherein oxygen is introduced into a jet tube along with the other gases so as to provide a stable flame when ignited. The invention can be used with either means for producing a flow of the gas to be analyzed, a highly flammable gas, and oxygen. It is only required that means for igniting the gases be located far enough downstream for the gases to form a combustible mixture and that means be provided for sensing a temperature related to that produced when the gases are ignited by the ignition means. Prior to such ignition, the air is flowing at a normal rate and the gases have a temperature that may have different values depending on the temperature which the gases acquire in passing through other parts of the detector. Means are provided for responding to a sudden increase in the temperature to start gradually reducing the ratio of oxygen to hydrogen below its normal value, regardless of how these gases reach the jet, and restore the ratio to its normal value when the temperature drops to the value it had when the reduction in the ratio of oxygen to hydrogen commenced.

What is claimed is:

1. A flame ionization detector, comprising
   means for forming a jet from gases to be analyzed and a flammable gas, when said gases are applied thereto,
   mixing means for introducing air to the periphery of the jet when air is applied thereto,
   a collector tube having one end mounted so as to receive gases from the jet,
   an exit tube for exhausting gases from said collector tube, said exit tube having one end inserted into the other end of said collector tube,
   electrical insulating means inserted between said exit tube and said collector tube,
   a filament igniter mounted within said collector tube and having its ends respectively connected to said collector tube and said exit tube,
   an electrical conductor connected between said exit tube and said collector tube so that it, the exit tube and the filament form a closed electrical loop,
   a magnetic core linking said loop,
   a winding linking said core,
   a transformer having primary and secondary windings, said secondary winding being coupled to said winding for linking said core for causing alternating electrical current to flow through said winding when said primary winding is energized,
   a current sensing resistor connected in said circuit with said transformer so that alternating current flows through it when said transformer is energized,
   a source of direct current potential and an electrometer connected between said collector tube and said means for forming the jet so as to collect ions produced when the jet is ignited and produce a current proportional to the rate at which ions are collected,
   means responsive to the voltage across said resistor for causing said mixing means to reduce the flow of air when said voltage changes by a given amount at a rate exceeding a predetermined value, and
   means responsive to the voltage across said resistor for causing said mixing means to restore the flow of air to its former value when said voltage reverts to the value it had when the air was shut off.

2. A flame ionization detector, comprising
   inlet means adapted to be connected to sources of gas to be analyzed, a flammable gas and air,
   means coupled to said inlet means for forming a flow of a mixture of the gases which, when ignited, will burn with a steady flame,
   ion collecting means located downstream in said flow from said means for forming a flow,
   an electrometer coupled to said ion collecting means for deriving an indication corresponding to the rate at which ions are collected,
   gas igniting means located downstream in said flow from said means for forming a flow, means for generating an electrical signal corresponding to the temperature of gases in said flow at a point near said gas igniting means, valve means connected to said air inlet means for adjusting the flow of air therethrough, means for causing said valve means to reduce the flow of air through said inlet means when the electrical signal indicates that the temperature has increased by a given amount and at a rate in excess of a given value, and means for causing said valve means to increase the flow of air through said inlet means when the electrical signal indicates that the temperature has decreased by a given amount which may differ from said given amount.

3. A flame ionization detector as set forth in claim 2 wherein means are provided for preventing said valve control means from reducing the flow of air to said inlet means when said electrometer indicates that the rate at which ions are collected exceeds a predetermined value.

4. A flame ionization detector as set forth in claim 2 wherein said means for adjusting the flow of air through said inlet means includes a pneumatic capacitor and a valve for connecting it to a supply of air and wherein said control means operates said valve.

5. A flame ionization detector, comprising means for forming a jet from gas to be analyzed, flammable gas and gas including oxygen when these gases are supplied to inlet means thereof, the gases in said jet flowing in a given direction, means for collecting ions which are formed in said jet from gas to be analyzed when the jet is burning, an electrometer coupled to said means for collecting ions so as to give an indication as to the rate at which ions are formed, gas ignition means mounted downstream in said jet from said means for forming said jet and separated from the flame produced when said jet is burning, and means responsive to the temperature in the vicinity of said gas ignition means for decreasing the flow of the gas including oxygen into said inlet means in response to an increase in temperature and for increasing the flow of the gas including oxygen into said inlet means in response to a decrease in temperature.

* * * * *